(12) United States Patent
Murofushi et al.

(10) Patent No.: US 7,550,449 B2
(45) Date of Patent: Jun. 23, 2009

(54) CARBA CYCLIC PHOSPHATIDIC ACID DERIVATIVE

(75) Inventors: Kimiko Murofushi, 4-12-17, Tsuji, Minami-ku, Saitama-shi, Saitama, 336-0026 (JP); Mutsuko Mukai, Hyogo (JP); Susumu Kobayashi, Tokyo (JP); Hiromu Murofushi, Saitama (JP)

(73) Assignee: Kimiko Murofushi, Saitama-shi (JP)

( * ) Notice: Subject to any disclaimer, the term of this patent is extended or adjusted under 35 U.S.C. 154(b) by 343 days.

(21) Appl. No.: 10/516,315

(22) PCT Filed: Jun. 10, 2003

(86) PCT No.: PCT/JP03/07335

§ 371 (c)(1),
(2), (4) Date: Jan. 30, 2006

(87) PCT Pub. No.: WO03/104246

PCT Pub. Date: Dec. 18, 2003

(65) Prior Publication Data

US 2006/0122155 A1    Jun. 8, 2006

(30) Foreign Application Priority Data

Jun. 11, 2002   (JP) .............................. 2002-169743

(51) Int. Cl.
*A61K 31/66* (2006.01)
(52) U.S. Cl. ........................ 514/109; 554/78
(58) Field of Classification Search ................... 554/78; 514/109
See application file for complete search history.

(56) References Cited

U.S. PATENT DOCUMENTS

| 5,238,965 | A | 8/1993 | Piazza et al. |
| 6,150,345 | A | 11/2000 | Chun et al. |
| 2004/0176329 | A1 | 9/2004 | Murofushi et al. |
| 2004/0214799 | A1* | 10/2004 | Mukai et al. ................ 514/109 |
| 2004/0220149 | A1 | 11/2004 | Murofushi et al. |

FOREIGN PATENT DOCUMENTS

| JP | 5-230088 | 9/1993 |
| JP | 6-228169 | 8/1994 |
| JP | 7-149772 | 6/1995 |
| JP | 7-258278 | 10/1995 |
| JP | 9-025235 | 1/1997 |
| WO | 99/047101 | 9/1999 |
| WO | 00/009139 | 2/2000 |
| WO | 00/057864 | 10/2000 |
| WO | 00/057865 | 10/2000 |
| WO | 02/083148 | 10/2002 |
| WO | 02/083149 | 10/2002 |
| WO | 02/094286 | 11/2002 |

OTHER PUBLICATIONS

Kawai et al. publication, Synthesis and Physiological Effects of Cyclic Lysophosphatidic Acid and Carba-Derivative, "The 23rd symposium on Progression Organic Reactions in Life Science,"Nov. 17 and 18, 1997, The Pharmaceutical Society of Japan, pp. 1-9 (English-translated version).*
Kawai et al. publication, Synthesis and Physiological Effects of Cyclic Lysophosphatidic Acid and Carba-Derivative, "The 23rd symposium on Progression Organic Reactions in Life Science,"Nov. 17 and 18, 1997, The Pharmaceutical Society of Japan, pp. 101-104.*
Liliom et al., 1996, CAS: 125:265929.*
English language Abstract of JP 5-230088, published Sep. 7, 1993.
English language Abstract of JP 6-228169, published Aug. 16, 1994.
English language Abstract of JP 7-149772, published Jun. 13, 1995.
English language Abstract of JP 7-258278, published Oct. 9, 1995.
English language Abstract of JP 9-25235, published Jan. 28, 1997.
W.H. Moolenaar, Exp. Cell. Res., vol. 253, pp. 230-238, 1999.
Z. Guo et al., Proc. Natl. Acad. Sci. USA, vol. 93, pp. 14367-14372, 1996.
Hecht, J. et al., J. Cell Biol., vol. 135, pp. 1071-1083, 1996.
S. An et al., J. Biol. Chem., vol. 273, pp. 7906-7910, 1998.
K. Bandoh et al., J. Biol. Chem., vol. 274, pp. 27776-27785, 1999.
D.-S. Im et al., Mol. Pharmacol., vol. 57, pp. 753-759, 2000.
Van Corven, E., et al., Cell, vol. 59, pp. 45-54, 1989.
Umansky, S. R. et al., Cell Death Diff., vol. 4, pp. 608-616, 1997.
A. Gohla et al., J. Biol. Chem., vol. 273, pp. 4653-4659, 1998.
Tigyi, G. et al., J. Biol. Chem., vol. 267, pp. 21360-21367, 1992.
Jalink, K. et al., Cell Growth & Differ., vol. 4, pp. 247-255, 1993.
Jalink, K. et al., J. Cell Biol., vol. 126, pp. 801-810, 1994.
Tigyi, G. et al., J. Neurochem., vol. 66, pp. 537-548, 1996.

(Continued)

*Primary Examiner*—Rei-tsang Shiao
(74) *Attorney, Agent, or Firm*—Greenblum & Bernstein, P.L.C.

(57) ABSTRACT

It is an object of the present invention to synthesize a carba cyclic phosphatidic acid derivative having a novel structure by substituting O at position sn-2 of the glycerol skeleton with $CH_2$, and study the action of the obtained derivative to suppress cancer cell invasion. The present invention provides a compound represented by the following formula (I):

$$\begin{array}{c} \text{O} \\ \| \\ CH_2-O-C-R \\ | \\ CH-CH_2 \\ | \quad\quad\searrow\text{O} \\ \quad\quad P \\ CH_2-O \nearrow \quad \searrow OM \end{array} \quad (I)$$

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups may comprise a cycloalkane ring or aromatic ring; and M represents a hydrogen atom or counter cation.

6 Claims, 1 Drawing Sheet

OTHER PUBLICATIONS

Imamura, F. et al., Biochem. Biophys. Res. Commun., vol. 193, pp. 497-503, 1993.
K. L. O'Connor et al., J. Cell. Biol., vol. 143, pp. 1749-1760, 1998.
J. C. Stam et al., EMBO J., vol. 17, pp. 4066-4074, 1998.
Murakami-Murofushi, K. et al., J. Biol. Chem., vol. 267, pp. 21512-21517, 1992.
Kobayashi, T. et al., Life Sciences, vol. 65, pp. 2185-2191, 1999.
Liliom, K. et al., Am. J. Physiol., vol. 274, pp. C1065-1074, 1998.
Murakami-Murofushi, K. et al., Cell Struct. Funct., vol. 18, pp. 363-370, 1993.
P. L. Hordijk et al., J. Biol. Chem., vol. 269, pp. 3534-3538, 1994.
L. R. Howe et al., J. Biol. Chem., vol. 268, pp. 20717-20720, 1993.
T. Kobayashi et al., Protein, Nucleic Acid and Enzyme, vol. 44, pp. 1118-1125, 1999.
Mukai, M. et al., Int. J. Cancer, vol. 81, pp. 918-922, 1999.
Akedo, H. et al., Cancer Res., vol. 46, pp. 2416-2422, 1986.
M. Mukai et al., FEBS Letters, vol. 484, pp. 69-73, 2000.
Karoly Liliom et al., "N-Palmitoly-serince and N-Palmitoyl-tyrosine Phosphoric Acids Are Selective Competitive Antagonists of the Lysophosphatidic Acid Receptors", Molecular Pharmacology, vol. 50, No. 3, pp. 616-623 (1996).
Tsutomu Yokomatsu et al., "Lipase-Catalyzed Enantioselective Acylation of Prochiral 2-(ω-Phosphono)alkyl-1,3-Propanediols: Application to the Enantioselective Synthesis of ω-Phosphono-α-Amino Acids", Tetrahedron: Asymmetry, vol. 7, No. 9, pp. 2743-2754 (1996).
Schumacher, K. A. et al., Thromb. Haemostas., vol. 42, pp. 631-640, 1979.
Tokumura, A. et al., Lipids, vol. 13, pp. 468-472, 1978.
Fischer, D. J. et al., Mol. Pharmacol., vol. 54, pp. 979-988, 1998.
Imamura, F. et al., Jpn. J. Cancer Res., vol. 82, pp. 493-496, 1991.
Imamura, F. et al., Int. J. Cancer, vol. 65, pp. 627-632, 1996.
Shiono, S. et al., Biochem. Biophys. Res. Commun., vol. 193, pp. 667-673, 1993.
Murakami-Murofushi, K. et al., Biochem. Biophys. Acta, vol. 1258, pp. 57-60, 1995.
Sakurai, Y. et al., J. Neurosci. Res., vol. 52, pp. 17-26, 1998.
Banker, G. A. et al., Brain Research, vol. 126, pp. 397-425, 1977.
Yokomatsu, T. et al., Heterocycles, vol. 46, pp. 463-472, 1997.
Bestmann, H. J. et al., Chemical Ber., vol. 0.125, pp. 225-229, 1992.
Chemical Abstracts, vol. 105, abstract No. 191524, 1986.
S. Kobayashi et al., Tetrahedron Letters, vol. 34, pp. 4047-4050, 1993.
"The 23$^{rd}$ Symposium on Progression Organic Reactions in Life Science," Nov. 17 and 18, 1997, The Pharmaceutical Society of Japan, Synthesis and Physiological Action of Cyclic Phosphatidic Acid and Carba Derivative, Abstract Collection pp. 101-104.
Kawai et al., Synthesis and Physiological Effects of Cyclic Lysophosphatidic Acid and Carba Derivative "The 23$^{rd}$ Symposium on Progression Organic Reactions in Life Science," Nov. 17 and 18, 1997, The Pharmaceutical Society of Japan, pp. 1-9, which appears to be an English translation of the above-cited "The 23$^{rd}$ Symposium on Progression Organic Reactions in Life Science".
C. Laudanna et al., J. Biol. Chem., vol. 272, pp. 24141-24144, 1997.
J.-M. Dong et al., J. Biol. Chem., vol. 273, pp. 22554-22562, 1998.
G. Poste et al., Nature, vol. 283, pp. 139-146, 1980.
M. Mukai et al., Protein, Nucleic Acid and Enzyme, vol. 44, pp. 1126-1131, 1999.
Kobayashi et al., CAS: 123:144502, 1995.
Shinagawaga et al., CAS: 124:76506, 1995.
Uchiyama et al., Biochimica et Biophysica Act, 1771 (2007) 103-112.
Liliom, Molecular Biology, 1996, 50(3), 616-623.
Phosphate—Wikipedia, the free encyclopedia, 4 pages, downloaded from http://en.wikipedia.org/wiki/Phosphates, on Jan. 13, 2009.
Kobayashi et al., Tetrahedron Letters, vol. 34, No. 25, 4047-4050, 1993.

* cited by examiner

CARBA CYCLIC PHOSPHATIDIC ACID DERIVATIVE

TECHNICAL FIELD

The present invention relates to a carba cyclic phosphatidic acid derivative, and a medicament using the same.

BACKGROUND ART

Lysophosphatidic acid (LPA) has the simplest structure among phospholipids which compose the biological membrane, wherein either fatty acid at the sn-1 or -2 position of glycerol in phosphatidic acid (PA) is deacylated (FIG. 1). In a normal cell, the LPA ratio of all phospholipids is as extremely low as 0.5% or less. By the 1980s, LPA was believed to be merely an intermediate or a degradation product of phospholipid biosynthesis. However, recently, various physiological activities of LPA have been shown (Moolenaar, W. H.: Exp. Cell Res. 253, 230-238 (1999)). Furthermore, the presence of several receptors on the cell membrane has also been revealed (Guo, Z., et al., Proc. Natl. Acad. Sci. USA 93, 14367-14372 (1996); Hecht, J. H., et al., J. Cell Biol. 135, 1071-1083 (1996); An, S., et al., J. Biol. Chem. 273, 7906-7910 (1998); Bandoh, K., et al., J. Biol. Chem. 274, 27776-27785 (1999); and Im, D-S., et al., Mol. Pharmacol. 57, 753-759 (2000)). LPS is now attracting attention as a functional phospholipid.

LPA is known to induce various actions depending on cell type. In addition to the promotion of cell proliferation (van Corven, E. J., et al, Cell 59, 45-54 (1989)) and the suppression of cell death (Umansky, S. R., et al, Cell Death Diff. 4, 608-616 (1997)), LPA guides changes in the cytoskeleton by activating the signal transduction system via Rho which is a low-molecular-weight G protein, and induces the stress fiber formation in fibroblasts (Gohla, A., et al., J. Biol. Chem. 273, 4653-4659 (1998)), the degeneration of neurite in nerve cells (Tigyi, G. et al., J. Biol. Chem. 267, 21360-21367 (1992); Jalink, K., et al., Cell Growth & Differ. 4, 247-255 (1993); Jalink, K., et al., J. Cell Biol. 126, 801-810 (1994); and Tigyi, G. et al., J. Neurochem. 66, 537-548 (1996)), the invasion of cancer cell (Imamura, F., et al., Biochem. Biophym. Res. Commun. 193, 497-503 (1993); O'Connor, K. L., et al., J. Cell Biol. 143, 1749-1760 (1998); and Stam, J. C., et al., EMBO J. 17, 4066-4074 (1998)) and the like.

In 1992, a fat-soluble substance that suppresses the activity of DNA polymerase α, a DNA replication enzyme of eukaryotic cells, and suppresses the proliferation of animal culture cells was discovered, isolated and purified from mixoamoeba, the haploid of *Physarum polycephalum* slime molds (Murakami-Murofushi, K., et al., J. Biol. Chem. 267, 21512-21517 (1992)). It has been shown that, in this substance, hexadecanoic acid containing cyclopropane is bound at the sn-1 position of the glycerol backbone, and phosphoric acid is bound via cyclic ester bond at the sn-2 and -3 positions of the glycerol backbone (FIG. 1). This substance is named PHYLPA since it is a Physarum-derived LPA-like substance.

Since PHYLA has a characteristic fatty acid at the sn-1 position, a derivative was chemically synthesized by substituting the fatty acid with a general fatty acid, and its activity was studied. As a result, it was shown that all substances suppress cell proliferation while they differ in their suppression degrees. Thus it was revealed that the anti-proliferative action of PHYLPA results from the cyclic phosphate group at the sn-2 and -3 positions. At present, these LPA analogs having such cyclic phosphate group are generically called cPA, cyclic phosphatidic acid (FIG. 1). cPA has been recently detected in the form of being bound to albumin in a human serum (Kobayashi, T., et al., Life Sciences 65, 2185-2191 (1999)), revealing that cPA is broadly present in the living world. Moreover, the cPA in a lipid fraction separated at this time mainly consists of Pal-cPA having palmitic acid as fatty acid. The presence of cPA has also been confirmed in the rat and pig brains in addition to being present in sera. Tigyi et al. have also detected a group of LPA analogues containing cPA in the aqueous humour or lacrimal gland fluid of a rabbit model of corneal damage (Liliom, K., et al., Am. J. Physiol. 274, C1065-C1074 (1998)).

cPA has been revealed to exhibit various physiological activities similar to or contrary to those of LPA. While LPA promotes the proliferation of culture cells, cPA exhibits suppression action (Murakami-Murofushi, K., et al, Cell Struct. Funct. 18, 363-370 (1993)). This action is reversible. When cPA is removed from a medium, cells begin to proliferate again. Two possibilities have been suggested as the mechanism for anti-proliferative action.

In mouse fibroblasts (NIH3T3), it has been found that cPA causes a rise in intracellular cAMP concentration within several minutes. This phenomenon disappears by blocking the rise in intracellular $Ca^{2+}$ concentration (Murakami-Murofushi, K., et al, Cell Struct. Funct. 18, 363-370 (1993)), suggesting a possibility that cPA may activate $Ca^{2+}$-dependent adenylate cyclase via receptors on the cell membrane. It has been shown that a rise in intracellular cAMP concentration suppresses the activation of MAP kinase (Hordijk, P. L., et al, J. Biol. Chem. 269, 3534-3538 (1994); and Howe, L. R., et al, J. Biol. Chem. 268, 20717-20720 (1993)), suggesting that this may lead to the inhibition of proliferation. On the other hand, it is considered that cPA is easily incorporated within cells because of its structure. Regarding this point, cPA having the sn-1 position labeled with fluoresence was synthesized and added to cells, and then its behavior was observed. As a result, it has been revealed that cPA rapidly penetrates into the cells, and is localized in the peripheral portion of the nucleus in the cytoplasm. Furthermore, it has also been found that cPA inhibits, in vitro, Cdc25 phosphatase activity which controls the cell cycle (Tetsuyuki KOBAYASHI and Kimiko MUROFUSHI: Protein, Nucleic Acid and Enzyme, 44, 1118-1125 (1999)). Accordingly, it is also possible that cPA inhibits the cell proliferation by directly suppressing the activation of Cdk2 kinase complex in the cytoplasm without involving receptors on the cell membrane.

Moreover, in fibroblasts cultured in a medium with a limited serum level, both LPA and cPA induce stress fiber formation by actin monomers within the cells (Tetsuyuki KOBAYASHI and Kimiko MUROFUSHI: Protein, Nucleic Acid and Enzyme, 44, 1118-1125 (1999)). In this case, similar to LPA, cPA is considered to initiate its action by activating Rho via the binding to a cell membrane receptor.

Furthermore, regarding the invasion of cancer cells, cPA exhibits strong suppressing activity in contrast to the promotion action of LPA (Mukai, M., et al, Int. J. Cancer 81, 918-922 (1999)).

Cancer metastasis is the most significant phenomenon showing malignancy of tumor, and is established through complex steps. In particular, the invasion is a characteristic step. Cancer cells which were released from the primary lesion in vivo invade stroma and blood vessels. The cells are then transported via the blood stream, invade outside the blood vessels and further invade remote organs, in which the cells then start proliferation to form a metastatic lesion. To analyze in vitro this phenomenon, AKEDO et al. have modeled peritoneal invasion that was developed when rat ascites hepatoma cells (AH-130) were implanted in the rat abdominal cavity, and thus have developed an experimental system with which the migration of cancer cells across the normal host cell layer can be quantitatively evaluated (Akedo, H., et al, Cancer Res. 46, 2416-2422 (1986)). Normally, an experimental system for observing cancer cells that pass through the membrane coated with extracellular substrates is used to study invasion. In contrast to such method, this system is thought to well reflect an in vivo state. Some cancer cells to be used for this experimental system need serum but some of them do not need any serum for invasion. A highly invasive clone (MM1) of AH-130 cells requires serum for its invasion. As a result of search for an invasion-promoting substance in serum, it was revealed that LPA is at least one of such invasion-promoting substances (Imamura, F., et al, Biochem. Biophys. Res. Commun. 193, 497-503 (1993)). Accordingly, the effect of cPA, a structural analog of LPA, on the invasion was examined. As a result, it was found that cPA suppresses invasion, completely contrary to the case of LPA. Some derivatives having different fatty acids bound at sn-1 position were synthesized, and their invasion inhibitory activities were examined. As a result, Pal-cPA exhibited the strongest invasion suppressing activity. Furthermore, in the same assay system, Pal-cPA significantly suppressed the invasion of human fibrosarcoma cells (HT-1080) which require neither serum nor LPA for their invasion (Mukai, M., et al., Int. J. Cancer 81, 918-922 (1999)).

Also in MM1 cells, intracellular cAMP concentration was elevated within several minutes by the addition of Pal-cPA, and this effect was not lost even during co-existence with LPA (Mukai, M., et al, Int. J. Cancer 81, 918-922 (1999)). When a reagent which can increase the intracellular cAMP concentration was added, LPA-induced invasion was suppressed. Moreover, it was shown that LPA-mediated Rho activation is inhibited by the addition of these reagents or Pal-cPA (Mukai, M., et al., FEBS Letters 484, 69-73 (2000)). These results suggest that also in this cancer cell (MM1), cPA may inhibit Rho activity via activation of cAMP-dependent Protein Kinase A (A kinase) by increasing an intracellular cAMP concentration, so as to suppress invasion.

DISCLOSURE OF THE INVENTION

The present inventors had previously synthesized a cyclic phosphatidic acid derivative by substituting O at position sn-3 of the glycerol skeleton with $CH_2$. They had demonstrated that this derivative is able to suppress cancer cell invasion (Japanese Patent Application No. 2001-150685). In the present invention, the present inventors have synthesized a carba cyclic phosphatidic acid derivative having a novel structure by substituting O at position sn-2 of the glycerol skeleton with $CH_2$, and they have studied the action of the obtained derivative to suppress cancer cell invasion. Thus, it is an object of the present invention to provide a novel medicament based on the aforementioned studies.

The present inventors have conducted intensive studies directed towards synthesizing the aforementioned carba cyclic phosphatidic acid derivative having a novel structure. They performed an Arbuzov reaction, using, as a raw material, an iodide compound synthesized by the method of Dubois et al. (Dubois J. et al., Tetrahedron 47, 1001 (1991)), so as to synthesize (2,2-dimethyl-[1,3]dioxan-5-ylmethyl)-phosphonic acid dimethyl ester. Subsequently, they allowed this compound to react with methanol and p-toluenesulfonic acid hydrate, so as to synthesize (2-methoxy-2-oxo-215-[1,2]oxaphospholan-4-yl)methanol. The present inventors further allowed this compound to react with a desired fatty acid for esterification, and thus, they succeeded in synthesizing a cyclic phosphatidic acid derivative having a structure wherein O at position sn-2 of the glycerol skeleton is substituted with $CH_2$. The aforementioned synthetic pathway is a novel synthetic pathway, which has not been reported. The obtained carba cyclic phosphatidic acid derivative was evaluated in an in vitro invasion assay system in terms of activity of suppressing cancer cell invasion. As a result, it was demonstrated that the carba cyclic phosphatidic acid derivative of the present invention has activity of suppressing cancer cell invasion. The present invention has been completed based on these findings.

Thus, the present invention provides a compound represented by the following formula (I):

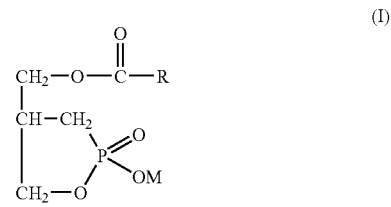

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups may comprise a cycloalkane ring or aromatic ring; and M represents a hydrogen atom or counter cation.

In the formula (I), R is preferably $-C_{15}H_{31}$, $-(CH_2)_7CH=CHC_6H_{13}$, or $-(CH_2)_7CH=CHC_8H_{17}$.

In another aspect, the present invention provides a compound represented by the following formula (II):

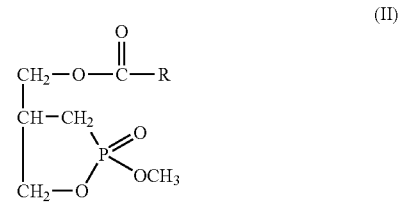

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups may comprise a cycloalkane ring or aromatic ring.

In another aspect, the present invention provides a compound represented by the following formula (III):

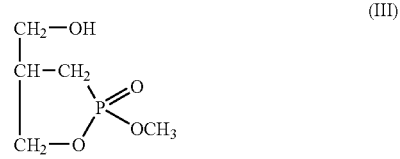

In another aspect, the present invention provides a compound represented by the following formula (IV):

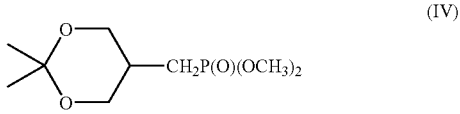

In another aspect, the present invention provides a medicament comprising, as an active ingredient, a compound represented by the following formula (I):

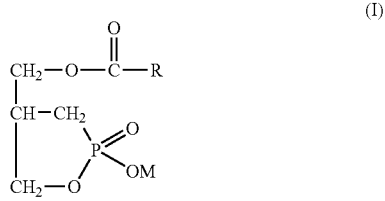

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups may comprise a cycloalkane ring or aromatic ring; and M represents a hydrogen atom or counter cation.

The medicament of the present invention can preferably be used as an anticancer agent, and can more preferably be used to suppress cancer cell invasion, so as to suppress metastasis of the cancer.

In another aspect, the present invention provides a method for suppressing cancer or metastasis of the cancer, which comprises administering a therapeutically effective amount of the compound represented by the above formula (I) to mammals including humans.

In another aspect, the present invention provides the use of the compound represented by the above formula (I) in production of medicaments (e.g. anticancer agents).

BEST MODE FOR CARRYING OUT THE INVENTION

Figure 1:
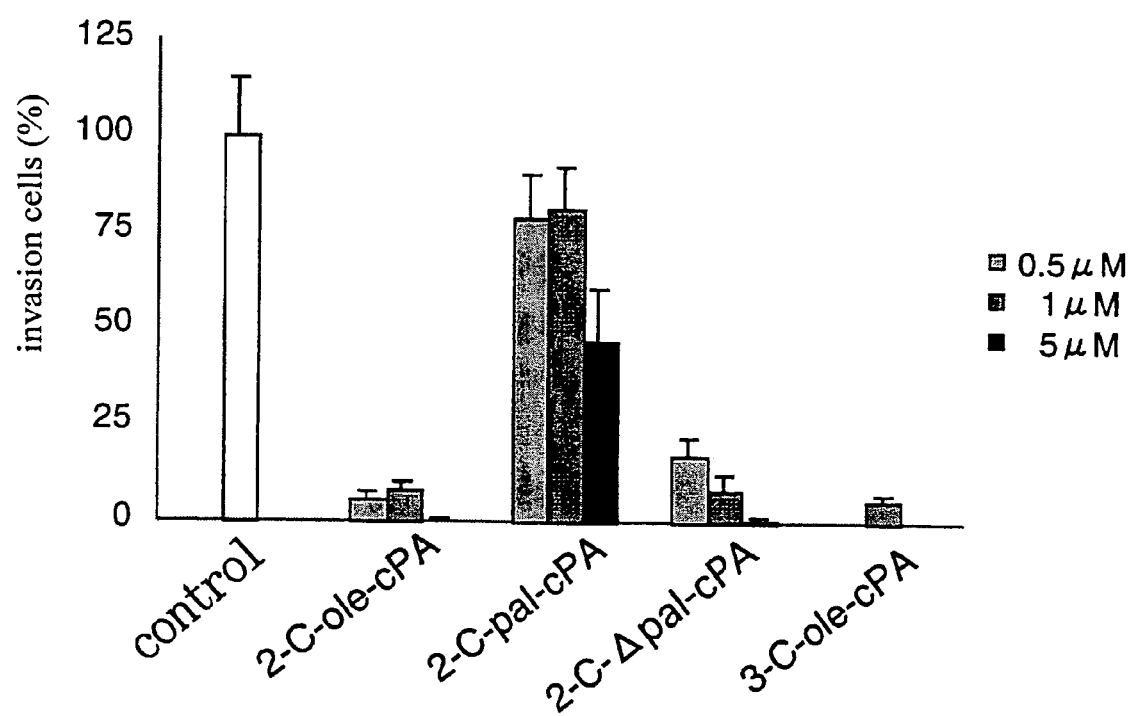
FIG. 1 shows the results obtained by examining the effects of a cPA synthetic derivative on invasion induced by LPA by in vitro invasion assay.

The embodiments of the present invention will be described in detail below.

The compound of the present invention is a carba cyclic phosphatidic acid derivative represented by the following formula (I):

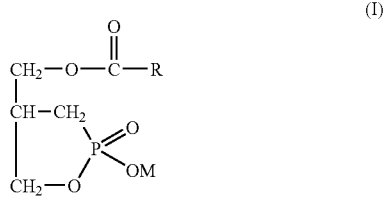

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups may comprise a cycloalkane ring or aromatic ring; and M represents a hydrogen atom or counter cation.

Examples of the $C_{1-30}$ linear or branched alkyl groups represented by the substituent R in the formula (I) include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group.

Examples of the $C_{2-30}$ linear of branched alkenyl group represented by the substituent R include an allyl group, a butenyl group, an octenyl group, a decenyl group, a dodecadienyl group, and a hexadecatrienyl group. More specifically, the examples include 8-decenyl group, 8-undecenyl group, 8-dodecenyl group, 8-tridecenyl group, 8-tetradecenyl group, 8-pentadecenyl group, 8-hexadecenyl group, 8-heptadecenyl group, 8-octadecenyl group, 8-icocenyl group, 8-dococenyl group, heptadeca-8,11-dienyl group, heptadeca-8,11,14-trienyl group, nonadeca-4,7,10,13-tetraenyl group, nonadeca-4,7,10,13,16-pentaenyl group, and henicosa-3,6,9,12,15,18-hexaenyl group.

The examples of the $C_{2-30}$ linear or branched alkynyl group represented by the substituent R include 8-decynyl group, 8-undecynyl group, 8-dodecynyl group, 8-tridecynyl group, 8-tetradecynyl group, 8-pentadecynyl group, 8-hexadecynyl group, 8-heptadecynyl group, 8-octadecynyl group, 8-icocynyl group, 8-dococynyl group, and heptadeca-8,11 -diynyl group.

The examples of the cycloalkane ring which may be contained in the above described alkyl group, alkenyl group or alkynyl group include, for example, a cyclopropane ring, a cyclobutane ring, a cyclopentane ring, a cyclohexane ring, and a cyclooctane ring. The cycloalkane ring may contain one or more hetero atoms, and examples thereof include an oxylane ring, an oxetane ring, a tetrahydrofuran ring, and an N-methylprolidine ring.

The examples of an aromatic ring which may be contained in the above described alkyl group, alkenyl group or alkynyl group include, for example, a benzene ring, a naphthalene ring, a pyridine ring, a furan ring, and a thiophene ring.

Accordingly, in the case where the substituent R is an alkyl group substituted with a cycloalkane ring, the examples include a cyclopropylmethyl group, a cyclohexylethyl group, and an 8,9-methanopentadecyl group.

In the case where the substituent R is an alkyl group substituted with an aromatic ring, the examples include a benzyl group, a phenetyl group, and a p-pentylphenyloctyl group.

M in the cyclic phosphatidic acid (cPA) derivative represented by the formula (I) is a hydrogen atom or a counter cation. In the case where M is a counter cation, examples thereof include an alkali metal atom, an alkali earth metal atom, and a substituted or unsubstituted ammonium group. The alkali metal atom includes, for example, lithium, sodium and potassium. The alkali earth metal atom includes, for example, magnesium and calcium. The substituted ammonium group includes, for example, a butylammonium group, a triethylammonium group and a tetramethylammonium group.

The present invention also relates to a compound represented by the above formula (II) (wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups may comprise a cycloalkane ring or aromatic ring), a compound represented by the following formula (III), and a compound represented by the following formula (IV).

The compounds represented by the formulas (II), (III), and (IV) are useful as synthetic intermediates of the compound of the present invention represented by formula (I).

With regard to the compound represented by the formula (I), isomers such as a positional isomer, geometric isomer, tautomer, or optical isomer may exist depending on the type of a substituent thereof. All these possible isomers and a mixture consisting of two or more types of such isomers at a certain ratio are also included in the scope of the present invention.

In addition, the compound represented by the formula (I) may be in the form of an adduct consisting of the compound and water or various types of solvents (hydrates or solvates). Such an adduct is also included in the scope of the present invention. Moreover, any given crystal forms of the compound represented by the formula (I) and a salt thereof are also included in the scope of the present invention.

The compound of the present invention represented by the formula (I) can be synthesized through a synthetic pathway described below, which is also described later in the examples in the present specification. However, this synthetic pathway is provided only as an example of the synthesis of the compound of the present invention. Thus, compounds produced through other synthetic pathways are also included in the scope of the present invention.

(1) First Process

An iodide compound synthesized by the method of Dubois et al. (Dubois J. et al., Tetrahedron, 47, 1001 (1991)) (which corresponds to iodide compound 1 in examples described later) is used as a starting compound. Trimethyl phosphite is added to iodide compound 1, and the obtained mixture is heated under reflux for an appropriate period of time (for example, several hours to several days). During the reaction, trimethyl phosphite is further added, so that the reaction can be continued under reflux. After completion of the reaction, the reaction solution is left to cool. It is then subjected to vacuum distillation, so as to eliminate residual trimethyl phosphite. The residue is purified by common methods (for example, silica gel column chromatography, elution with chloroform:methanol=15:1), so as to obtain (2,2-dimethyl-[1,3]dioxan-5-ylmethyl)-phosphonic acid dimethyl ester (that is, the compound represented by formula (IV)).

(2) Second Process

The (2,2-dimethyl-[1,3]dioxan-5-ylmethyl)-phosphonic acid dimethyl ester obtained in the aforementioned first process is dissolved in toluene, and methanol and p-toluenesulfonic acid hydrate are added thereto. The obtained mixture is heated under reflux for an appropriate period of time (for example, 30 minutes to 10 hours). The reaction solution is left to cool, and the solvent is then removed under reduced pressure. The obtained residue is purified by common methods (for example, silica gel column chromatography, elution with chloroform:methanol=15:1), so as to obtain (2-methoxy-2-oxo-215-[1,2]oxaphospholan-4-yl)methanol (that is, the compound represented by formula (III)).

(3) Third Process

The (2-methoxy-2-oxo-215-[1,2]oxaphospholan-4-yl)methanol obtained in the aforementioned second process is dissolved in dichloromethane, and DMAP, a fatty acid, and WSC are then added thereto. The obtained mixture is stirred for reaction. As a fatty acid used herein, a suitable fatty acid such as oleic acid, palmitin acid, or palmitoleic acid can be used, depending on the type of the substituent R in the compound represented by the formula (I). The reaction solution is diluted with methanol and washed with water, and organic layers are then extracted with ethyl acetate. The organic layers are dried, and the solvent is eliminated therefrom, so as to obtain a crude product. The crude product is purified by common methods (for example, silica gel column chromatography, elution with benzene:ethyl acetate=1:1), so as to obtain cyclic phosphonate (that is, the compound represented by formula (II)).

(4) Fourth Process

The cyclic phosphonate represented by the formula (II) obtained in the aforementioned third process is dissolved in dichloromethane, and TMSBr is added thereto at a low temperature (for example, −15° C.). The obtained mixture is stirred for an appropriate period of time. The reaction solution is extracted with cold ether, organic layers are dried, and the solvent is then removed. The obtained crude product is purified by common methods (silica gel column chromatography, elution with hexane: ethyl acetate=2:1 and then with chloroform:methanol=5:1), so as to obtain the carba cyclic phosphatidic acid derivative of the present invention that is represented by the formula (I).

The present invention further relates to a medicament comprising, as an active ingredient, the compound represented by the formula (I) as defined above. The medicament of the present invention can be used, for example, as an anticancer agent.

As an example of the use of the medicament of the present invention, it can be used to suppress cancer cell invasion, so as to suppress metastasis of the cancer.

Cancer metastasis comprises a multi-step process that begins with the detachment of cancer cells from the primary lesion, disruption of the extracellular matrix, invasion into blood vessels, invasion across the vascular endothelial cell layers, adhesion in the remote organ, and proliferation. Various factors are involved in these steps, and inhibitors of them are now attracting attention as a new agent for suppression of cancer metastasis. Above all, invasion is the most characteristic step in the phenomenon of metastasis. It is considered that a superior anticancer agent is very likely to be developed from the substances that suppress the invasion of cancer cell. The present invention provides a novel agent for suppression of cancer metastasis which can be used as an agent for suppression of the invasion of cancer cell.

"Cancer metastasis" in the present invention means the shifting and proliferation of cancer cells from one part of the body to another organ, apparatus or the like. Specifically, it means that cancer cells shift to a site remote from the primary lesion so as to form cancer through the circulation systems of blood and lymph.

The types of cancer to be treated by the medicament of the present invention are not particularly limited, and include all forms of benign and malignant tumors. Specific examples of cancer include, but are not limited to, malignant melanoma, malignant lymphoma, digestive organ cancer, lung cancer, esophageal cancer, gastric cancer, large bowel cancer, rectal cancer, colon cancer, ureteral neoplasm, gallbladder cancer, bile duct cancer, biliary tract cancer, breast cancer, liver cancer, pancreatic cancer, testicular tumor, maxillary cancer, tongue cancer, lip cancer, oral cavity cancer, pharyngeal cancer, laryngeal cancer, ovarian cancer, uterine cancer, prostate cancer, thyroid cancer, brain tumor, Kaposi's sarcoma, hemangioma, leukemia, polycythemia vera, ganglioneuroblastoma, retinoblastoma, myeloma, bladder tumor, sarcoma, osteosarcoma, myosarcoma, skin cancer, basal cell carcinoma, skin appendage carcinoma, cutaneous metastatic carcinoma and skin malignant melanoma.

Organs to which cancer easily spreads by metastasis differ slightly depending on the type of cancer. For example, it is known that breast cancer spreads by metastasis at a higher rate to the lungs, liver, bone and lymph glands; gastric cancer to the liver, lungs, bone and adrenal gland; and large bowel cancer to the liver, lungs, adrenal glands and the like. Examples of metastatic cancer include metastatic liver cancer, metastatic jejunal carcinoma, metastatic bone tumor, metastatic brain tumor, metastatic lung tumor, cutaneous metastatic carcinoma, metastatic costal tumor, metastatic ovarian cancer and the like. Preferably, the medicament of the present invention can be used to suppress such cancer metastasis, and is particularly useful as an agent for suppression of postoperative metastasis. Moreover, the medicament of the present invention is clinically an agent for suppression of recurrence of cancer, and is expected to prolong the survival period of patients and increase the survival rate.

When the medicament of the present invention is used as an anti-cancer agent, it can be used in combination with a known chemotherapy, a surgical treatment method, radiotherapy, hyperthermia, immunotherapy or the like. In particular, the anti-cancer effect of the medicament of the present invention can be further enhanced by combined use with a known anti-tumor agent and/or a substance that suppresses cancer metastasis. By the combined use with the anti-cancer agent of the present invention, the dose of a known anti-tumor agent and/or a cancer metastasis-suppressing substance to be administered can be reduced. Thus, side effects that are caused by these agents (e.g., leukopenia, thrombocytopia, bleeding, anaemia, anorexia, nausea, vomition, stomatitis, diarrhea, efflorescence, unhairing, pigmentation of skin, onset of fever, dullness, cephalalgia, liver functional impairment, proteinuria, edema and anaphylaxis) may be reduced.

The medicament of the present invention is preferably provided in the form of a pharmaceutical composition which comprises one or more pharmaceutically acceptable additives and the compound of the formula (I) as an active ingredient.

The medicament of the present invention can be administered in various forms, and the dosage forms may be peroral or parenteral (for examples, intravenous, intramuscular, subcutaneous or intracutaneous injection, rectal dosage, and permucosal dosage). Examples of the pharmaceutical composition suitable for peroral dosage include a tablet, a granule, a capsule, a powder, a solution, a suspension, and a syrup. Examples of the pharmaceutical composition suitable for parenteral dosage include an injection, an infusion, a suppository, and a percutaneous absorption agent. The dosage form of the medicament of the present invention is not limited to these. Furthermore, the medicament of the present invention can also be made into sustained release formulations by publicly known methods.

The type of the pharmaceutical additives used for producing the medicament of the present invention is not particularly limited, and can be suitably selected by a person skilled in the art. For examples, one can use an excipient, a disintegration agent or a disintegration auxiliary agent, a binder, a lubricant, a coating agent, a base, a solvent or a solubilizer, a dispersant, a suspension agent, an emulsifier, a buffer, an antioxidant, an antiseptic, an isotonic agent, a pH adjusting agent, a solving agent, and a stabilizer. Individual ingredients which are used for the above purposes are well known to a person skilled in the art.

Examples of the pharmaceutical additives usable for preparing a peroral preparation include an excipient such as glucose, lactose, D-mannitol, starch and crystalline cellulose; a disintegration agent or a disintegration auxiliary agent such as carboxymethyl cellulose, starch and carboxymethyl cellulose calcium; a binder such as hydroxypropyl cellulose, hydroxypropyl methylcellulose, polyvinyl pyrrolidone, and gelatin; a lubricant such as magnesium stearate and talc; a coating agent such as hydroxypropyl methylcellulose, white sugar, polyethylene glycol and titanium oxide; a base such as Vaseline, liquid paraffin, polyethylene glycol, gelatin, kaolin, glycerin, purified water, and hard fat.

Examples of the pharmaceutical additives which can be used for preparing an injection or an infusion preparation include a solvent or a solubilizer which can be used for an aqueous injection or a use-time dissolution type injection such as injection distilled water, physiological saline, and propylene glycol; an isotonic agent such as glucose, sodium chloride, D-mannitol, and glycerin; and a pH adjusting agent such as an inorganic acid, an organic acid, an inorganic base and an organic base.

The medicament of the present invention can be administered to a mammal including human.

The dose of the medicament of the present invention should be increased or decreased according to the conditions such as age, sex, body weight, symptom of a patient, and dosage route. The dose of the active ingredient per day for an adult is generally 1 μg/kg to 1,000 mg/kg, and preferably 10 μg/kg to 10 mg/kg. The agent of the dose as mentioned above may be administered once a day, or may be dividedly administered a few times (for example, about 2-4 times) a day.

The present invention will be described in detail with reference to the following Examples, but the present invention is not limited by the Examples.

EXAMPLES

Synthetic Example 1

(1) Synthesis of (2,2-dimethyl-[1,3]dioxan-5-ylmethyl)-phosphonic acid dimethyl ester

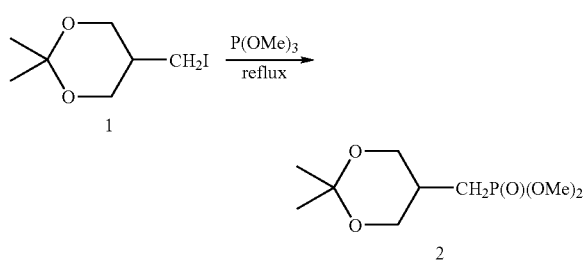

Using iodide compound 1 synthesized by the method of Dubois et al. (Dubois J. et al., Tetrahedron 47, 1001 (1991)) as a starting material, an Arbuzov reaction was carried out.

8.6 ml of trimethyl phosphite was added to iodide compound 1 (1.12 g, 4.62 mmol), and the mixture was heated under reflux at 130° C. for 14 hours. 8.6 ml of trimethyl phosphite was further added thereto, and the mixture was further refluxed for 6 hours. Thereafter, 8.6 ml of trimethyl phosphite was further added thereto, and the mixture was further refluxed for 3 hours. The reaction solution was left to cool. It was then subjected to vacuum distillation, so as to eliminate residual trimethyl phosphite. The residue was purified by silica gel column chromatography (chloroform:methanol=15:1), so as to obtain phosphonic acid 2 (986 mg, 90%). The obtained phosphonic acid 2 was directly used in the following reaction.

Rf value: 0.33 (Hexane:AcOEt=1:1)
$^1$H-NMR (270 MHz)
d: 1.42 (s, 6H, IP)
1.81 (dd, 2H, J=18.87, 6.93 Hz, C$\underline{H}_2$P(O)(OMe)$_2$)
1.92-2.21 (m, 1H, H-2)
3.66 (dd, 2H, J=12.05, 7.10 Hz, H-3)
3.78 (d, 6H, J=11.22 Hz, P(O)(OC$\underline{H}_3$)$_2$)
4.02 (dd, 2H×½, J=11.87, 1.32 Hz, H-3)
4.17 (dd, 2H×½, J=14.68, 7.09 Hz, H-3)

(2) Synthesis of (2-methoxy-2-oxo-2λ5-[1,2]oxaphospholan-4-yl)methanol

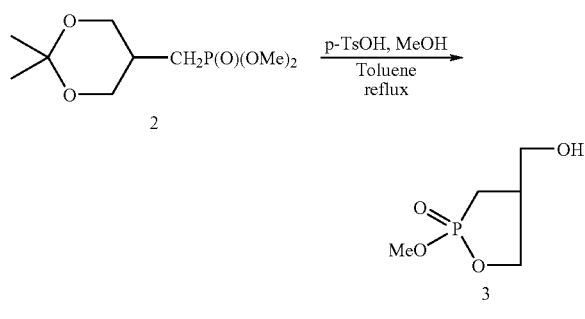

Phosphonic acid 2 (76.4 mg, 0.32 mmol) was dissolved in 3.8 ml of toluene, and 0.13 ml of methanol and 14.0 mg (0.23 eq) of p-toluenesulfonic acid hydrate were added thereto. The obtained mixture was heated under reflux for 2 hours and 45 minutes. Thereafter, the reaction solution was left to cool, and the solvent was removed under reduced pressure. The obtained residue was purified by silica gel column chromatography (chloroform:methanol=15:1), so as to obtain cyclic phosphonic acid 3 (40.3 mg, 76%).

Rf value: 0.57 (CHCl$_3$:MeOH=4:1)
$^1$H-NMR (300 MHz)
d: 1.73-2.12 (m, 2H, H-4)
2.69-2.87 (m, 1H, H-2)
3.66 (d, 2H, J=6.43 Hz, H-1)
3.78 (dd, 3H, J=0.55, 11.02 Hz, OCH$_3$)
3.83-4.40 (m, 2H, H-3)

(3) Synthesis of 9-octadecenoic acid 2-methoxy-2-oxo-2λ$^5$-[1,2]oxaphospholan-4-ylmethyl ester

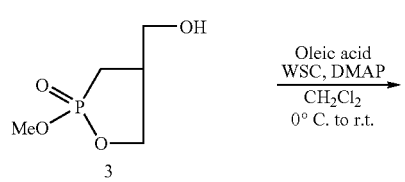

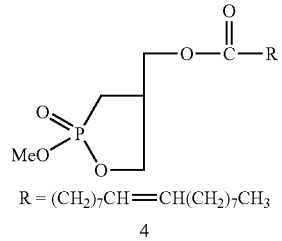

Cyclic phosphonic acid 3 (8.4 mg, 0.051 mmol) was dissolved in 3 ml of dichloromethane. DMAP (1.9 mg, 0.3 eq), oleic acid (18.6 mg, 1.3 eq), and WSC (19.4 mg, 2 eq) were added to the solution at a temperature of 0° C. The obtained mixture was stirred at room temperature for 1 day. The reaction solution was diluted with methanol and washed with water, and then, organic layers were extracted with ethyl acetate. The organic layers were dried over sodium sulfate, and the solvent was removed under reduced pressure. The obtained crude product was purified by silica gel column chromatography (benzene:ethyl acetate=1:1), so as to obtain cyclic phosphonate 4 (15.6 mg, 72%).

Likewise, the same above compound was allowed to react with palmitin acid or with palmitoleic acid, so as to obtain palmitate (R=(CH$_2$)$_{14}$CH$_3$, 89.7 mg, 51%) and palmitoleate (R=(CH$_2$)$_7$CH=CH(CH$_2$)$_5$CH$_3$, 89.6 mg, 35%).

4-1 oleate
Rf value: 0.23 (Benzene:AcOEt=1:1)
$^1$H-NMR (500 MHz)
d: 0.88 (t, 3H, J=6.87, H-18')
1.26-1.30 (m, 20H, H-4'-7',H-12'-17')
1.60-1.63 (m, 2H, H-3')
1.66-1.77 (m, 2H×½, H-4)
1.99-2.03 (m, 4H, H-8',H-11')
2.04-2.13 (m, 2H×½, H-4)
2.32 (t, 2H, J=7.48 Hz, H-2')
2.82-2.99 (m, 1H, H-2)
3.80 (dd, 3H, J=11.14, 4.12 Hz, OCH$_3$)
3.76-4.35 (m, 4H, H-1,H-3)
5.31-5.38 (m, 2H, H-9',H-10')

4-2 palmitate
Rf value: 0.25 (Hexane:AcOEt=1:2)
$^1$H-NMR (400 MHz)
d: 0.88 (t, 3H, J=6.83 Hz, H-16')
1.25-1.28 (m, 24H, H-4'-15')
1.59-1.63 (m, 2H, H-3')
1.67-1.78 (m, 2H×½, H-4)
1.98-2.13 (m, 2H×½, H-4)
2.32 (t, 2H, J=7.55 Hz, H-2')
2.83-2.92 (m, 1H, H-2)
3.80 (dd, 3H, J=11.23, 3.16 Hz, OCH$_3$)
3.94-4.36 (m, 4H, H-1,H-3)

4-3 palmitoleate
$^1$H-NMR (500 MHz)
d: 0.88 (t, 3H, J=6.83 Hz, H-16')
1.28-1.30 (m, 16H, H-4'-7',H-12'-15')
1.60-1.61 (m, 2H, H-3')
1.65-1.78 (m, 2H×½, H-4)
2.01-2.02 (m, 4H, H-8',H-11')
2.05-2.13 (m, 2H½, H-4)
2.32 (t, 2H, J=7.43 Hz, H-2')
2.84-2.96 (m, 1H, H-2)
3.80 (dd, 3H, J=11.09, 3.30 Hz, OCH$_3$)
3.72-4.36 (m, 4H, H-1,H-3)
5.30-5.39 (m, 2H, H-9',H-10')

(4) Synthesis of 9-octadecenoic acid 2-hydroxy-2-oxo-2λ⁵-[1,2]oxaphospholan-4-ylmethyl ester

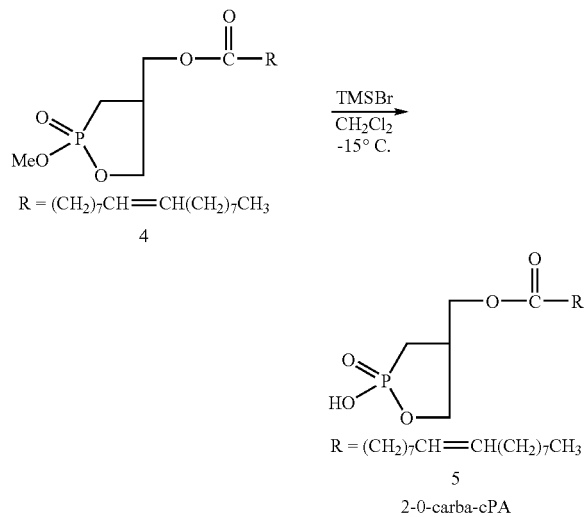

Cyclic phosphonate 4 (33.3 mg, 0.077 mmol) was dissolved in 4 ml of dichloromethane, and TMSBr (35.5 mg, 3 eq) was added thereto at −15° C. The obtained mixture was stirred for 4.5 hours. The reaction solution was mixed to ice water, and then extracted once with cold ether. The organic layers were dried over sodium sulfate, and the solvent was removed under reduced pressure. The obtained crude product was purified by silica gel column chromatography (hexane:ethyl acetate=2:1→chloroform:methanol=5:1), so as to obtain 2-O-carba-cPA 5 (12.1 mg, 38%).

Likewise, the same above compound was allowed to react with palmitate (R=(CH$_2$)$_{14}$CH$_3$) or with palmitoleate (R=(CH$_2$)$_7$CH=CH(CH$_2$)$_5$CH$_3$), so as to obtain palmitate (3.5 mg, 10%) and palmitoleate (3.4 mg, 8%) of 2-O-carba-cPA 5.

5-1 2-O-carba-cPA oleate
Rf value: 0.26 (CHCl$_3$:MeOH:H$_2$O=60:20:3)
$^1$H-NMR (500 MHz) d: 0.88 (t, 3H, J=6.88 Hz, H-18')
1.26-1.30 (m, 20H, H-4'-7',H-12'-17')
1.60-1.61 (m, 2H, H-3')
1.70-1.77 (m, 2H×½, H-4)
1.99-2.03 (m, 4H, H-8',H-11')
2.04-2.09 (m, 2H½, H-4)
2.31 (t, 2H, J=7.48 Hz, H-2')
2.90-2.91 (m, 1H, H-2)
3.92-4.29 (m, 4H, H-1,H-3)
5.31-5.38 (m, 2H, H-9',H-10')

5-2 2-O-carba-cPA palmitate
$^1$H-NMR (400 MHz) d: 0.88 (t, 3H, J=6.71 Hz, H-16')
1.26 (m, 24H, H-4'-15')
1.59-1.63 (m, 2H, H-3')
1.70-1.80 (m, 2H×½, H-4)
2.04-2.13 (m, 2H×½, H-4)
2.31 (t, 2H, J=7.63 Hz, H-2')
2.86-2.96 (m, 1H, H-2)
3.91-4.32 (m, 4H, H-1,H-3)

5-3 2-O-carba-cPA palmitoleate
$^1$H-NMR (500 MHz) d: 0.88 (t, 3H, J=6.85 Hz, H-16')
1.26-1.30 (m, 16H, H-4'-7',H-12'-15')
1.61 (m, 2H, H-3')
1.70-1.78 (m, 2H×½, H-4)
1.99-2.03 (m, 4H, H-8',H-1')
2.05-2.12 (m, 2H×½, H-4)
2.31 (t, 2H, J=7.65 Hz, H-2')
2.85-2.95 (m, 1H, H-2)
3.91-4.31 (m, 4H, H-1,H-3)
5.31-5.38 (m, 2H, H-9',H-10')

Test Example 1

(Materials and Methods)

Cell Culture

The abdominal cavity of a 300-g male Donryu rat (Nippon Seibutsu Zairyo) was aseptically opened. The obtained mesentery was treated with 0.25% trypsin at 37° C. for 15 minutes. The resultant product was filtrated through a 150 μm stainless mesh, and the filtrate was then centrifuged, so as to recover mesothelial cells. A medium was formed by adding 10% FBS to Eagle's MEM1 (Nissui), to which Eagle's MEM amino acid vitamin medium (Nissui) had been added at twice the amount thereof. The above cells were cultured in the obtained medium at 37° C. under 5% CO$_2$. The cells were cultured for 1 week. Thereafter, the monolayer mesothelial cells, which became confluent, were used for invasion assay.

MM1 cells, which are highly invasive clones of a rat ascites hepatoma cell line (AH-130), have been established by Mukai et al. (Int. J. Cancer 81, 918-922 (1999)). MM1 cells were also cultured under the same conditions as those used for mesothelial cells.

In vitro Invasion Assay

In vitro invasion assay has been developed by Akedo et al. (Cancer Res. 46, 2416-2422 (1986)). MM1 cells were subjected to multilayer culture on mesothelial cells, which had grown until they became confluent, in the presence of 25 μM LPA (SIGMA). Various types of cPA shown in FIG. 1 were added thereto. The cells were cultured for 20 hours at 37° C. under 5% CO$_2$. Thereafter, the cells were immobilized with 10% formalin, and the number of colonies of invaded MM1 cells was counted using a phase contrast microscope. In FIG. 1, 2-C-ole-cPA indicates 2-O-carba-cPA oleate, 2-C-pal-cPA indicates 2-O-carba-cPA palmitate, 2-C-Δpal-cPA indicates 2-O-carba-cPA palmitoleate, and 3-C-ole-cPA (comparative example) indicates 3-O-carba-cPA oleate.

cPA and LPA were cooled on ice in PBS containing 0.1% fatty-acid free BSA (SIGMA). They were then sonicated for emulsification, and conserved at −20° C. before use.

(Results)

The results are shown in FIG. 1. The effects of a cPA synthetic derivative on invasion (transcellular migration) induced by LPA were studied. As a result, as shown in FIG. 1, it was found that 2-C-cPA, wherein O at position sn-2 of the glycerol skeleton is substituted with CH$_2$, suppresses invasion to the same degree as 3-C-cPA, wherein O at position sn-3 of the glycerol skeleton is substituted with CH$_2$. In addition, among natural cPAs, those wherein palmitic acid binds to position sn-1 suppress invasion most strongly. However, among 2-C-cPAs, those to which oleic acid or palmitoleic acid containing a double bond binds suppress invasion more strongly than those to which palmitic acid binds, as in the case of 3-C-cPA.

INDUSTRIAL APPLICABILITY

The present invention provides a carba cyclic phosphatidic acid derivative having a novel structure wherein O at position sn-2 of the glycerol skeleton is substituted with CH$_2$. The carba cyclic phosphatidic acid derivative of the present invention has action to suppress cancer cell invasion, and thus, it is useful for a medicament such as an anticancer agent.

The invention claimed is:

1. A compound represented by the following formula (I):

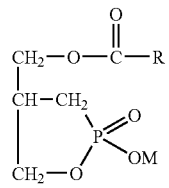

(I)

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups are optionally substituted with a cycloalkane ring or aromatic ring; and M represents a hydrogen atom or counter cation.

2. The compound according to claim 1 wherein, in the formula (I), R is $-C_{15}H_{31}$, $-(CH_2)_7CH=CHC_6H_{13}$, or $-(CH_2)_7CH=CHC_8H_{17}$.

3. A compound represented by the following formula (II):

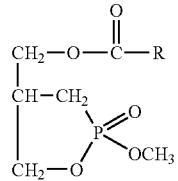

(II)

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups are optionally substituted with a cycloalkane ring or aromatic ring.

4. A compound represented by the following formula (III):

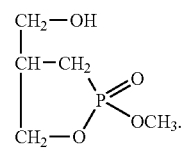

(III)

5. A compound represented by the following formula (IV):

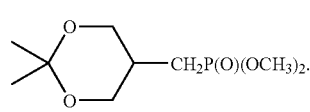

(IV)

6. A medicament composition comprising, as an active ingredient, a compound represented by the following formula (I):

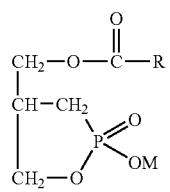

(I)

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, wherein these groups are optionally substituted with a cycloalkane ring or aromatic ring; and M represents a hydrogen atom or counter cation.

* * * * *